United States Patent [19]

Calverley et al.

[11] Patent Number: 5,378,695

[45] Date of Patent: Jan. 3, 1995

[54] VITAMIN D ANALOGUES

[75] Inventors: Martin J. Calverley; Kai Hansen, both of Herlev; Lise Binderup, Tastrup, all of Denmark

[73] Assignee: Leo Pharmaceutical Products Ltd. A/S (Lovens Kemiske Fabrik Produktionsaktieselskab), Ballerup, Denmark

[21] Appl. No.: 62,154

[22] Filed: May 17, 1993

Related U.S. Application Data

[63] Continuation of Ser. No. 721,563, filed as PCT/DK90/00037, Feb. 13, 1990, abandoned.

[30] Foreign Application Priority Data

Feb. 23, 1989 [GB] United Kingdom ............... 8904153

[51] Int. Cl.[6] ........................................... C07C 401/00
[52] U.S. Cl. ..................................... 514/167; 552/653
[58] Field of Search ..................... 552/653; 514/167

[56] References Cited

FOREIGN PATENT DOCUMENTS 0184112  6/1986  European Pat. Off. .

OTHER PUBLICATIONS

Murayama, et al. "Synthetic studies of vitamin $D_3$ analogues-VIII-Synthesis of 22-oxavitamin $D_3$ analogues". *Chem. Pharm. Bull.* vol. 34, No. 10, pp. 4410–4413 (1986).

Abe, et al. "Synthetic analogues of vitamin $D_3$ with an oxygen atom in the side chain skeleton" *FEB* 05407, vol. 226, No. 1, pp. 58–62 (Dec. 1987).

Chemical Abstracts, vol. 108, No. 11, Mar. 1988, Junko et al, "Synthetic Analogs of Vitamin D3 with an oxygen atom in the side chain skelton." see abstract 8819v, & FEBS Lett. 1987, 226 (1) 58–62.

Chemical Abstracts, vol. 110, No. 2, Jan. 1989, Katsuhito et al.: "Antitumor pharmaceuticals containing 9, 10–seco–5, 7, 10 (19)–pregnatriene derivatives." see abstracts 13599s & Jpn Kokai Tokkyo Koho JP 63107930, May 1988.

*Primary Examiner*—Johann Richter
*Assistant Examiner*—Kimberly J. Kestler
*Attorney, Agent, or Firm*—Cushman, Darby & Cushman

[57] ABSTRACT

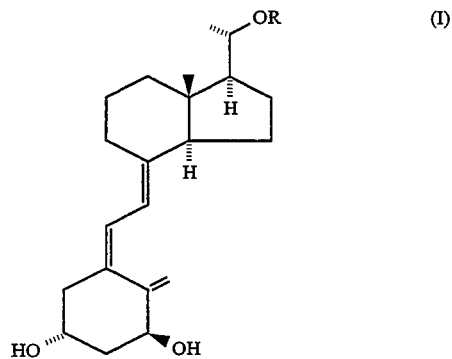

The present invention relates to compounds of formula (I), in which formula R stands for an alkyl group containing from 7 to 12 carbon atoms optionally substituted with a hydroxy group; and derivatives of the compounds of formula (I) in which one or more hydroxy groups have been transformed into —O-acyl or —O-glycosyl or phosphate ester groups, such masked groups being hydrolyzable in vivo, in pure form or in mixtures. The present compounds find use in both the human and veterinary practice in the treatment and prophylaxis of autoimmune diseases, including diabetes mellitus, hypertension, inflammatory diseases such as rheumatoid arthritis and asthma as well as diseases characterized by abnormal cell differentiation and/or cell proliferation, and/or imbalance in the immune system.

8 Claims, No Drawings

VITAMIN D ANALOGUES

This is a continuation of application Ser. No. 07/721,563, filed as PCT/DK90/00037, Feb. 13, 1990, which was abandoned upon the filing hereof.

This invention relates to a hitherto unknown class of compounds which shows an immunomodulating effect as well as strong activity in inducing differentiation and inhibiting undesirable proliferation of certain cells, including skin cells, to pharmaceutical preparations containing these compounds, to dosage units of such preparations, and to their use in the treatment and prophylaxis of autoimmune diseases, including diabetes mellitus, hypertension, inflammatory diseases such as rheumatoid arthritis and asthma as well as diseases characterized by abnormal cell differentiation and/or cell proliferation, and/or imbalance in the immune system.

The compounds of the present invention are represented by the general formula I

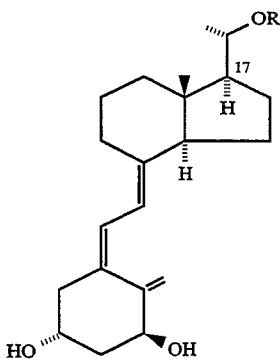

in which formula R stands for an alkyl group containing from 7 to 12 carbon atoms optionally substituted with a hydroxy group.

Preferably R is a group of formula II

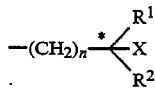

where n is an integer from 1 to 7; $R^1$ and $R^2$, which may be the same or different, stand for hydrogen, lower alkyl, lower cycloalkyl, or taken together with the carbon atom (starred in formula II) bearing the group X, $R^1$ and $R^2$ can form a $C_3$-$C_8$ carbocyclic ring; X stands for hydroxy or hydrogen.

In the context of this invention, the expression "lower alkyl" indicates a straight or branched saturated or unsaturated carbon chain containing from 1 to 5 carbon atoms, and the expression "lower cyclo-alkyl" indicates a saturated or unsaturated $C_3$-$C_7$ carbocyclic ring.

As can be seen from formula I and II, depending on the meanings of R, X, $R^1$ and $R^2$, the compounds of the invention can comprise several diastereoisomeric forms (e.g. R or S configuration at the starred carbon atom). The invention covers all these diastereoisomers in pure form and also mixtures of diastereoisomers. In addition, derivatives of I in which one or more of the hydroxy groups are masked as groups which can be reconverted to hydroxy groups in vivo are also within the scope of the invention ("bioreversible derivatives or prodrugs of I").

The term "bioreversible derivatives or prodrugs of I" includes, but is not limited to, derivatives of the compounds of formula I in which one or more hydroxy groups have been transformed into —O-acyl or —O-glycosyl groups, or a phosphate ester, such masked groups being hydrolyzable in vivo.

The compounds I in which R is not substituted with hydroxy are another type of prodrug. These compounds are relatively inactive in vitro, but are converted to active compounds of formula I by enzymatic hydroxylation after administration to the patient.

It has recently been shown that $1\alpha,25$-dihydroxyvitamin $D_3$ ($1,25(OH)_2D_3$) influences the effects and/or production of interleukins, indicating the potential use of this compound in the treatment of diseases characterized by a dysfunction of the immune system, e.g. autoimmune diseases and rejection of transplants. In addition, other conditions characterized by an abnormal interleukin-1 production, e.g. inflammatory diseases such as rheumatoid arthritis may be treated with $1,25(OH)_2D_3$.

It has also been shown that $1,25(OH)_2D_3$ is able to stimulate the differentiation of cells and inhibit excessive cell proliferation, and it has been suggested that this compound might be useful in the treatment of diseases characterized by abnormal cell proliferation and/or cell differentiation such as psoriasis.

Also, the use of $1,25(OH)_2D_3$ for the treatment of hypertension and diabetes mellitus has been suggested.

However, the therapeutic possibilities in such indications of $1,25(OH)_2D_3$ are severely limited by the well known potent effect of this hormone on calcium metabolism; elevated blood concentrations will rapidly give rise to hypercalcemia. Thus, this compound and its potent synthetic analogues are not completely satisfactory for use as drugs in the treatment of e.g. psoriasis, cancer or immune diseases which may require continuous administration of the drug in relatively high doses.

The 22-oxa-analogues of $1\alpha$-hydroxyvitamin $D_3$ and $1\alpha,25$-dihydroxyvitamin $D_3$ and are described in E. Murayama et al, Chem. Pharm. Bull., 34, 4410 (1986), J. Abe et al, FEBS LETTER, 226, 58 (1987) and European Patent Application, publication number 184 112.

In vitro experiments indicate that a 22-oxa analogue may have advantageous properties. Thus $1\alpha,25$-dihydroxy-22-oxavitamin $D_3$ is reported to have only one 14th as much affinity as $1\alpha,25(OH)_2D_3$ for the chick intestinal cytosolic receptor, a weaker affinity than $1,25(OH)_2D_3$ for the receptor in a human myeloid leukemia cell line (HL-60), but high activity as an inducer of differentiation in HL-60 cells.

The usefulness of a vitamin D analogue in the above mentioned indications is dependent not only upon a favourable ratio of binding affinity to relevant receptors compared to the intestinal receptor, but also upon the fate of the compound in the organism.

These known 22-oxa compounds are characterized by having a side chain (the substituent on C-17 (confer formula I) whose size (total number of carbon atoms) does not exceed that in $1,25$-$(OH)_2D_3$ itself (i.e. 8 carbon atoms). We have now found to our surprise that the analogues of type I having at least 7 carbon atoms in the group R (i.e. a total of at least 9 carbon atoms in the side chain) exhibit a combination of metabolic stability, favourable selectivity with respect to the binding affinities to various receptors, and reduced calcemic effects which makes them significantly superior to the hereto known 22-oxa compounds.

The selectivity of the compounds of the invention is illustrated by the fact that while they have high affinities for the receptor in tumour cells (similar to or better than that of 1,25(OH)$_2$D$_3$) and the concentration needed to induce cell differentiation in a human monocytic tumour cell line is the same as or lower than that needed of 1,25(OH)$_2$D$_3$ to give the same effect, their binding affinity for the intestinal receptor is much lower than that of 1,25(OH)$_2$D$_3$. In vivo in rats the compounds are considerably less active than 1,25(OH)$_2$D$_3$ in inducing hypercalciuria and hypercalcemia.

For example, direct comparison (cf. Biochem. Pharmacol. 1988, 37, 889) of the compound I of Example 1 with 22-oxa-1,25(OH)$_2$D$_3$ has shown that the former is more potent an inhibitor of the proliferation of U937 cells, binds less strongly to the rachitic chick intestinal receptor, and is less potent in its calcemic effects as reflected by the concentration required to elevate serum calcium concentration in normal rats.

This renders the compounds of the invention especially suited for both local and systemic treatment and prophylaxis of human and veterinary disorders which are characterized by abnormal cell proliferation and/or cell differentiation, such as certain dermatological disorders including psoriasis and certain cancer forms, e.g. leukemia and myelofibrosis, and diseases characterized by an imbalance in the immune system, e.g. autoimmune diseases, and to obtain desired immunosuppression as in transplantation procedures, as well as treatment of acne, diabetes mellitus and hypertension and inflammatory diseases, such as rheumatoid arthritis and asthma. As the compounds of this invention may promote the differentiation of the hair follicle cells, these compounds may be used in the treatment of alopecia.

The compounds of formula I may conveniently be prepared from the vitamin D-derivative 1 (or its 20R isomer) (Tetrahedron, 43, 4609 (1987)) by the routes outlined in Scheme 1. Oxidation of 1 for example using the van Rheenen procedure (Tetrahedron Letters, 1969, 985) gives the ketone 2, which is reduced to the 20S-alcohol 3. When a suitable chiral reducing agent (for example an organoboron reagent) is used, 3 may be prepared stereoselectively, (cf. S. Masamune in "Stereochemistry of Organic and Bioorganic Transformations", ex W. Bartmann and K. B. Sharpless, eds., VCH, Weinheim, 1987, p. 60). Alternatively, 3 is conveniently prepared by NaBH$_4$ reduction of 2 and separating the co-produced major amount of corresponding 20R-alcohol chromatographically. O-Alkylation of 3 to give III is achieved by treatment under basic conditions with a side chain building block of general formula Z—R$^3$, in which Z is a leaving group such as a halogen (Cl, Br or I) or p-toluenesulphonyloxy or methanesulphonyloxy, and R$^3$ is R (of formula I) or optionally a radical which can be converted to R at any convenient later stage (or over several stages). Thus R$^3$ in compounds III, IV, V and VI does not necessarily have the same meaning along a particular synthetic sequence. The conversion of R$^3$ to R may well involve several steps and possibly involve a temporary protection of the sensitive triene system of the molecule. Apart from any necessary modification within the side chain (R$^3$), the conversion of III to I involves a photoisomerisation step and a desilylation step, analogous to the steps used in the last stages of the synthesis of other vitamin D analogues (see European patent No. 0 227 826).

The side chain building blocks, R$^3$Z, are either known compounds (several are described in international patent application PCT/DK89/00079) or may be prepared analogously to those described in PCT/DK89/00079. The R$^3$ is typically identical with formula II in which X is a protected OH group, e.g. tetrahydropyranyloxy or trialkylsilyloxy. (Any such THP ethers R$^3$Z, which are not described in PCT/DK89/00079, are readily prepared from the corresponding alcohol).

The following standard abbreviations are used throughout this disclosure: Me=methyl; Et=ethyl; Pr$^n$=n-propyl; Bu$^t$=tert-butyl; THP=tetrahydro-4H-pyran-2-yl; THF=tetrahydrofuran: Ts=p-toluenesulphonyl; TBA=tetra-(n-butyl)-ammonium.

Scheme 1

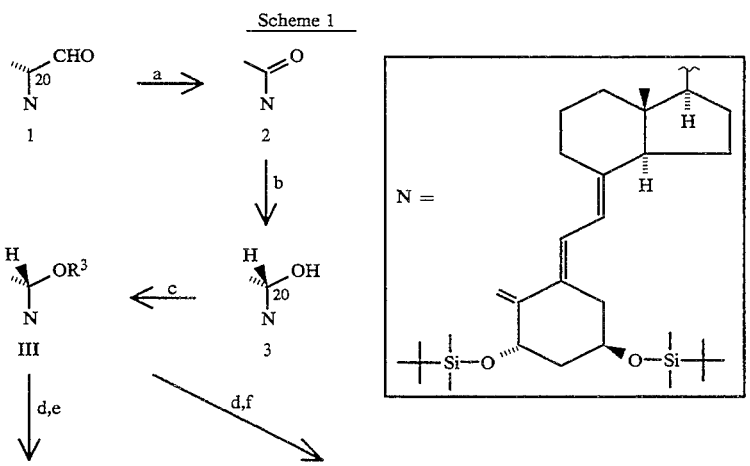

Scheme 1

-continued

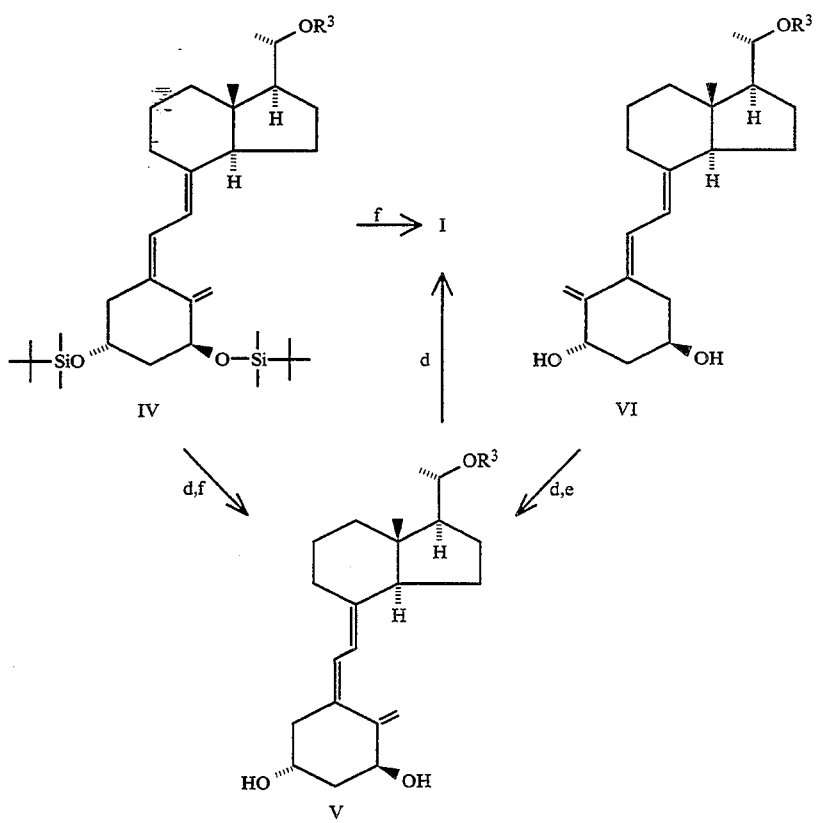

An alternative approach to the synthesis of compounds I via compounds IV of Scheme 1 is shown in Scheme 2. In this Scheme, the aldehyde 4 (Wovkulich et al, Tetrahedron 1984, 40, 2283) is degraded stereoselectively to the alcohol 8 via the intermediates shown. Alkylation of 8 to give VII is analogous to the reaction 3 → III of Scheme 1. Together with appropriate modification of $R^3$ (the meaning of which may be changed along the reaction sequence to a particular compound I), conversion of VII to VIII, Wittig coupling with the anion derived from IX (cf. Wovkulich, op. cit.) and deprotection gives the target compound I.

The compounds 3 and 8 are very versatile intermediates not only for the preparation of compounds I of the invention, but also for other analogues of formula I in which the group R is excluded from the present invention, such as the previously known 22-oxa-1,25-$(OH)_2D_3$. Indeed, we have conveniently used the reactions of both Schemes 1 and 2 for the synthesis of reference samples of 22-oxa-1,25-$(OH)_2D_3$ for direct biological comparison with the compounds of the invention.

Notes to Schemes 1 and 2 a) Oxidation with $O_2$ e.g. with $Cu(AcO)_2$, 2,2′-bipyridyl and 1,4-diazabicyclo[2,2,2]octane as catalyst.
b) Reduction (e.g. with $NaBH_4$).
c) Alkylation with the side chain building block $R^3$—Z in the presence of base (e.g. KOH, $KOBu^t$ or KH, with or without catalyst (e.g. 18-Crown-6) in solvent, e.g. THF).
d) Optional functional group modification in the side chain.
e) Isomerisation with hv-triplet sensitizer, e.g. anthracene.
f) Deprotection (e.g. with $TBA^+F^-$ or HF).
g) MeMgI or MeLi.
h) Oxidation (e.g. with pyridinium dichromate)
i) Baeyer-Villiger an oxidation (e.g. with m-chloroperbenzoic acid)
j) Hydrolysis or alcoholysis (e.g. KOH in MeOH).
k) (i) Desilylation (e.g. HF); (ii) Oxidation (e.g. pyridinium chlorochromate).
l) Reaction with the anion (e.g. lithio-derivative) derived by treating IX with an equivalent amount of base (e.g. n-BuLi).

It should be noted that although the shown intermediates may have hydroxyl groups protected as tert-butyl-dimethylsilyl ethers, the scope of the invention does not exclude the use of alternative hydroxyl protecting groups well known in the art (such as those described in T. W. Greene, "Protective groups in organic synthesis", Wiley, N.Y., 1981), together with alternative reactions for deprotection.

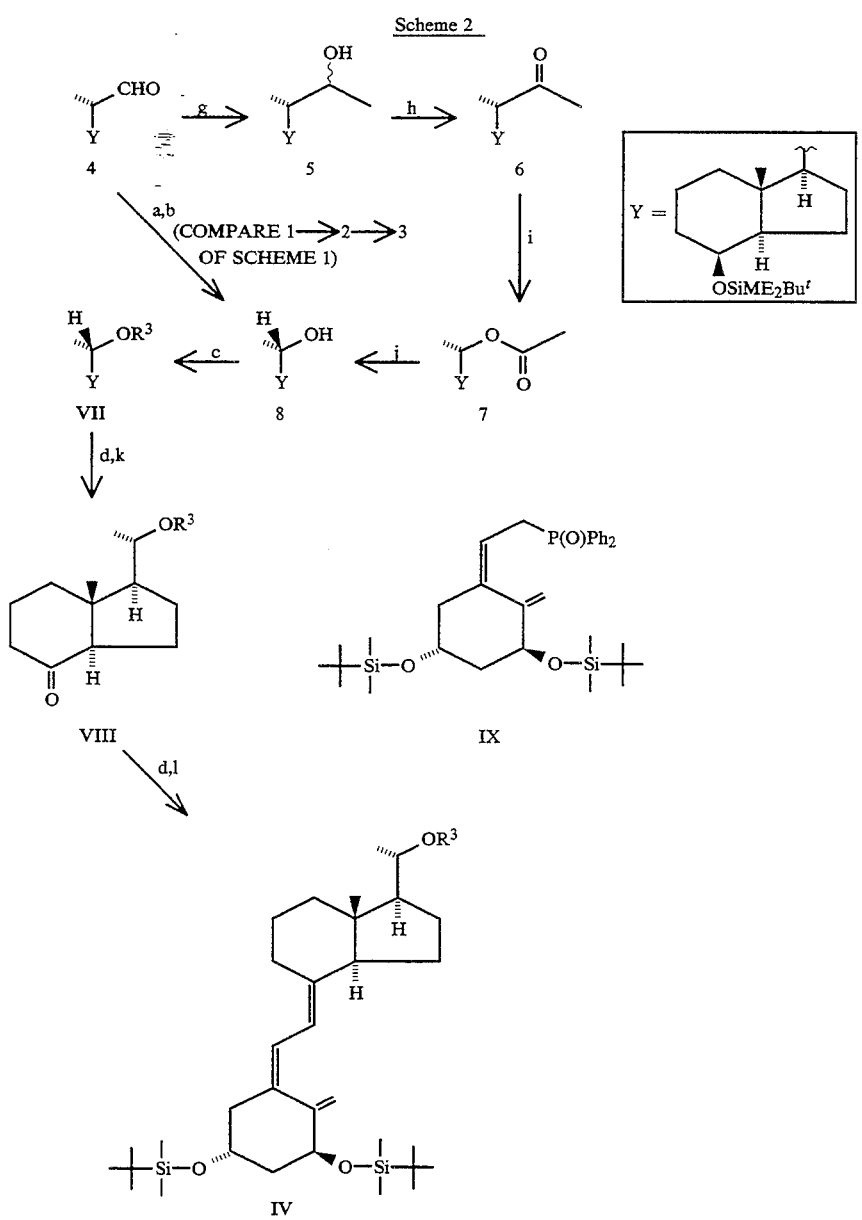

Scheme 2

The present compounds are intended for use in pharmaceutical compositions which are useful in the treatment of human and veterinary disorders as described above.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis, topical or enteral forms are preferred.

In the treatment of respiratory diseases like asthma an aerosol is preferred.

While it is possible for an active ingredient to be administered alone as the raw chemical, it is preferable to present it as a pharmaceutical formulation. Conveniently, the active ingredient comprises from 1 ppm to 0.1% by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, rectal, parenteral (including subcutaneous, intramuscular and intravenous), intra-articular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration include liquid or semi-liquid preparations such as liniments, lotions, applicants, oil-in-water or water-in-oil emulsions such as creams, ointments or pastes; or solutions or suspensions such as drops.

For asthma treatment inhalation of powder, self-propelling or spray formulations, dispensed with a spray can, a nebulizer or an atomizer can be used. The formulations, when dispensed, preferably have a particle size in the range of 10 to 100$\mu$.

Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more $C_1$–$C_6$-alkyl hydrocarbons or halogenated $C_1$–$C_6$-alkyl hydrocarbons or mixtures thereof; chlorinated and flourinated $C_1$–$C_6$-alkyl hydrocarbons are especially preferred. Generally, the propellant constitutes 45 to 99.9% w/w of the formulation whilst the active ingredient constitutes 1 ppm to 0.1% w/w, of the formulation.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including anti-oxidants), emulsifying agents and the like.

The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 1–1000 $\mu$g, preferably from 2–250 $\mu$g, of a compound of formula I are administered. In the topical treatment of dermatological disorders, ointments, creams or lotions containing from 1–1000 $\mu$g/g, and preferably from 10–500 $\mu$g/g, of a compound of formula I are administered. The oral compositions are formulated, preferably as tablets, capsules, or drops, containing from 0.5–500 $\mu$g, preferably from 1–250 $\mu$g, of a compound of formula I, per dosage unit.

The invention will now be further described in the following non-limiting Preparations and Examples:

PREPARATIONS AND EXAMPLES

General

The exemplified compounds I are listed in Table 1. The intermediates of Schemes 1 and 2 referred to in the Preparations are to be identified by numbers with the corresponding formulae in Table 2.

For nuclear magnetic resonance spectra (300 MHz) chemical shift values ($\delta$) are quoted for deuteriochloroform solutions relative to internal tetramethylsilane ($\delta=0$) or chloroform ($\delta=7.25$). The value for a multiplier, either defined (doublet (d), triplet (t), quartet (q)) or not (m) at the approximate mid point is given unless a range is quoted (s=singlet, b=broad). Coupling constants (J) are given in Hertz, and are sometimes approximated to the nearest unit.

Ether is diethyl ether, and was dried over sodium. THF was dried over sodium-benzophenone. Petroleum ether refers to the pentane fraction. Reactions were run at room temperature unless otherwise noted. The work-up procedure referred to involves dilution with the specified solvent (otherwise the organic reaction solvent), extraction with water and then brine, drying over anhydrous $MgSO_4$, and concentration in vacuo to give a residue.

TABLE 1

Exemplified Compounds I

| Compound Number | Example Number | Formula (II) | | | |
|---|---|---|---|---|---|
| | | n | $R^1$ | $R^2$ | X |
| 101 | 1 | 4 | Me | Me | OH |
| 102 | 2 | 3 | Et | Et | OH |
| 103 | 3 | 5 | Me | Me | OH |

TABLE 2

| Compound Number | Preparation Number | Formula | |
|---|---|---|---|
| | | Type (See Schemes) | $R^3$ |
| 9 | 5 | III | —$(CH_2)_4$—C(O—THP)$Me_2$ |
| 10 | 6 | III | —$(CH_2)_3$—C(OSiMe$_3$)Et$_2$ |
| 11 | 7 | III | —$(CH_2)_5$—C(OSiMe$_3$)Me$_2$ |
| 12 | 9 | IV | —$(CH_2)_4$—C(O—THP)$Me_2$ |
| 13 | 10 | IV | —$(CH_2)_3$—C(OSiMe$_3$)Et$_2$ |
| 14 | 11, 12 | IV | —$(CH_2)_5$—C(OSiMe$_3$)Me$_2$ |
| 15 | 8 | VII | —$(CH_2)_5$—C(OSiMe$_3$)Me$_2$ |

Preparation 1

Compound 2

To a solution of 1(S), 3(R)-bis-(tert-butyldimethylsilyloxy)-20(S)-formyl-9,10-secopregna-5(E),-(7E),10(19)-triene (Compound 1) (3.44 g, 6 mmol) in N,N-dimethylformamide (150 ml), 1,4-diazabicyclo[2.2.2]octane (600 mg, 5.3 mmol), cupric acetate, monohydrate (90 mg, 0.45 mmol) and 2,2'-bipyridyl (72 mg, 0.45 mmol) were added. Air was bubbled through the well stirred solution for 6 days at 40° C.

The reaction mixture was diluted with ethyl acetate (500 ml), extracted with water (2×100 ml) and saturated aqueous sodium chloride (3×50 ml) and dried over $MgSO_4$. Ethyl acetate was evaporated off, and the solid residue was purified by chromatography (silica gel, 10% ether in petroleum ether as eluant) to give the title compound.

NMR: δ=0.037 (s, 3H), 0.043 (s, 3H), 0.056 (s, 6H), 0.49 (s, 3H), 0.84 (s, 9H), 0.89 (s, 9H), 1.5–2.30 (m, 13H), 2.13 (s, 3H), 2.55 (dd, 1H), 2.70 (t, 1H), 2.89 (bd, 1H), 4.21 (m, 1H), 4.52 (m, 1H), 4.94 (m, 1H), 4.98 (m, 1H), 5.83 (d, 1H), 6.43 (d, 1H) ppm.

Preparation 2

Compound 3 and its 20R-isomer

Compound 2 (Prep. 1) (3.10 g, 5.5 mmol) was dissolved in tetrahydrofuran (140 ml) and sodium borohydride (0.35 g, 3.3 mmol) was added. Methanol was then added dropwise over 15 minutes. The reaction blend was stirred for 20 minutes, then diluted with ethyl acetate (560 ml). The solution was extracted with water (5×150 ml) and saturated aqueous sodium chloride (150 ml), dried over $MgSO_4$ and evaporated to give a colourless oil. The oily residue was purified by chromatography (silica gel, 15% ethyl acetate in petroleum ether as eluant). First eluted was the 20R-isomer:

NMR: δ=0.05 (m, 12H), 0.62 (s, 3H), 0.86 (s, 9H), 0.89 (s, 9H), 1.10–2.10 (m, 14H), 1.15 (d, 3H), 2.30 (bd, 1H), 2.53 (dd, 1H), 2.89 (m, 1H), 2.89 (m, 1H), 3.71 (m, 1H), 4.21 (m, 1H), 4.52 (m, 1H), 4.93 (m, 1H), 4.98 (m, 1H), 5.81 (d, 1H), 6.45 (d, 1H) ppm.

The fractions containing the more polar isomer (3) were evaporated to give a colourless residue which was crystallized from methanol.

NMR: δ=0.052 (bd, 12H), 0.54 (s, 3H), 0.85 (s, 9H), 0.89 (s, 9H), 1.22 (d, 3H), 1.20–2.10 (m, 14H), 2.30 (bd, 1H), 2.55 (dd, 1H), 2.87 (m, 1H), 3.72 (m, 1H), 4.21 (m, 1H), 4.52 (m, 1H), 4.94 (bs, 1H), 4.98 (m, 1H), 5.82 (d, 1H), 6.44 (d, 1H) ppm.

Preparation 3

Compound 8, via compounds 5, 6 and 7

A solution of compound 4 (3.1 g) in dry THF (30 ml) was treated dropwise with MeLi (1.5M in ether, 7 ml) with stirring at −40° C. After 10 minutes the reaction mixture was worked up (ether) to give crude 5 as a ca. 2:3 mixture of diastereoisomers [NMR: δ0.99 (minor isomer) and 1.13 (major isomer), (2d, total 3H, J =6.5)].

This was dissolved in dichloromethane (75 ml) and pyridinium dichromate (7 g) and TsOH (0.05 g) added. The mixture was stirred overnight and then diluted with ether (200 ml) and filtered through celite. The filtrate was concentrated in vacuo and purified by chromatography (silica gel, 5% ether in petroleum ether as eluant) to give 6 [NMR: δ inter alia 1.07 (d, 3H, J=7), 2.08 (s, 3H), 2.48 (m, 1H) and 3.99 (m, 1H)].

A solution of 6 (1 g), m-chloroperbenzoic acid (1.2 g) and TsOH (0.05 g) in dichloromethane (40 ml) was heated under reflux for 24 hours. After cooling, the mixture was diluted with ether and extracted consecutively with 5% sodium bicarbonate solution, 10% sodium sulphite solution, 5% sodium bicarbonate, and brine. Drying and concentration in vacuo gave a residue containing 7, which was directly hydrolysed by treatment of a solution in THF (5 ml) and methanol (20 ml) with a KOH solution (4N aqueous, 5 ml) at 50° C. for 1 hour. Work-up (dichloromethane) and purification by chromatography (silica gel; 40% ether in petroleum ether as eluant) gave 8 as an oil which crystallized on standing (M.p. 78°–80° C.).

NMR: δ=−0.02 and 0.00 (each s, 3H), 0.88 (s, 9H), 1.0–1.9 (m, 16H), 1.19 (d, 3H, J=6), 3.67 and 4.00 (each m, 1H).

Preparation 4

Compound 9

To a solution of compound 3 (169 mg, 0.3 mmol) in dry tetrahydrofuran (5 ml) potassium hydroxide (0.70 g, 10 mmol), 18-Crown-6 (40 mg) and 2-(6-bromo-2-methyl-2-hexyloxy)-tetrahydro-4H-pyran (Preparation 5) (1.7 g, 6 mmol) were added. The mixture was stirred vigorously overnight. The reaction mixture was filtered, and the filtrate evaporated in vacuo.

The residue was purified by chromatography (silica gel, 5% to 10% ether in petroleum ether as eluant) to give the title compound.

NMR: δ=0.055 (bs, 12H), 0.51 (s, 3H), 0.86 (s, 9H), 0.89 (s, 9H), 1.14 (d, 3H), 1.17 (s, 3H), 1.19 (s, 3H), 0.90–2.05 (m, 25H), 2.31 (bd, 1H), 2.54 (dd, 1H), 2.85 (m, 1H), 3.20 (m, 2H), 3.41 (m, 1H), 3.56 (m, 1H), 3.95

(m, 1H), 4.21 (m, 1H), 4.52 (m, 1H), 4.71 (m, 1H), 4.93 (bs, 1H), 4.98 (bs, 1H), 5.82 (d, 1H), 6.44 (d, 1H) ppm.

Preparation 5

2-(6-Bromo-2-methyl-2-hexyloxy)-tetrahydro-4H-pyran

To a stirred, ice-cooled solution of ethyl 5-bromopentanoate (18.7 ml) in dried ether (100 ml) was added dropwise over 1 hour a filtered solution of Grignard reagent, prepared from magnesium (10 g) and methyl iodide 25 ml) in dried ether (200 ml). After a further 30 minutes on the ice-bath, the reaction mixture was allowed to warm to room temperature over 30 minutes before being poured onto a stirred, ice-cooled solution of ammonium chloride (30 g) in water (200 ml). After the vigorous reaction had subsided, the ether layer was separated, and the aqueous layer was extracted with more ether. The combined ether layers were washed consecutively with water and saturated aqueous sodium chloride, dried, and concentrated in vacuo to give the crude intermediate (6-bromo-2-methyl-2-hexanol) as a pale yellow oil. This was dissolved in dichloromethane (100 ml), then 3,4-dihydro-2H-pyran (8.9 ml) and pyridinium p-toluenesulfonate (0.8 g) were added at room temperature. After 1 hour, the reaction solution was diluted with ether (250 ml) and extracted consecutively with saturated aqueous sodium hydrogen carbonate (150 ml), water (100 ml) and saturated aqueous sodium chloride (100 ml). After drying and removal of the solvent in vacuo, the product was purified by chromatography (150 g silica gel, 10% ether in petroleum ether as eluant) to give the desired compound as a colourless oil.

NMR: $\delta = 1.20$ (s, 3H), 1.22 (s, 3H), 1.40–1.95 (m, 12H), 3.42 (t, 2H), 3.45 (m, 1H), 4.72 (m, 1H) ppm.

Preparation 6

Compound 10

The compound was prepared using the procedure of Preparation 4, but replacing the 2-(6-bromo-2-methyl-2-hexyloxy)-tetrahydro-4H-pyran with an equivalent amount of 6-bromo-3-ethyl-3-(trimethylsilyloxy)hexane.

NMR in agreement with formula.

Preparation 7

Compound 11

The compound was prepared using the procedure of Preparation 4, but replacing the 2-(6-bromo-2-methyl-2-hexyloxy)-tetrahydro-4H-pyran with an equivalent amount of 7-bromo-2-methyl-2-(trimethylsilyloxy)heptane.

NMR in agreement with formula.

Preparation 8

Compound 15

The compound was prepared using the procedure of Preparation 7, but replacing compound 3 with compound 8 (150 mg).

NMR in agreement with formula.

Preparation 9

Compound 12

A solution of compound 9 (88 mg), anthracene (60 mg) and triethylamine (2 drops) in dichloromethane (10 ml) under $N_2$ in a Pyrex flask was irradiated with light from a high pressure ultra-violet lamp, type TQ 150Z2 (Hanau), at room temperature for 55 minutes. The solution was filtered, concentrated in vacuo, and the residue purified by chromatography (silica gel, 10% ether in petroleum ether as eluant) to give the title compound.

NMR: $\delta = 0.056$ (m, 12H), 0.50 (s, 3H), 0.86 (s, 9H), 0.87 (s, 9H), 1.14 (d, 3H), 1.17 (s, 3H), 1.19 (s, 3H), 1.0–2.0 (m, 25H), 2.21 (dd, 1H), 2.43 (m, 1H), 2.82 (m, 1H), 3.20 (m, 2H), 3.42 (m, 1H), 3.55 (m, 1H), 3.93 (m, 1H), 4.18 (m, 1H), 4.36 (m, 1H), 4.70 (m, 1H), 4.85 (bd, 1H), 5.17 (bd, 1H), 6.01 (d, 1H), 6.21 (d, 1H) ppm.

Preparation 10

Compound 13

The compound was prepared using the procedure of Preparation 9, but substituting compound 9 with compound 10.

NMR in agreement with structure.

Preparation 11

Compound 14

The compound was prepared using the procedure of Preparation 9, but substituting compound 9 with compound 11.

NMR in agreement with structure.

Preparation 12

Compound 14 (Alternative method)

A stirred solution of Compound 15 (90 mg) in ethyl acetate (0.5 ml) was treated with a mixture of acetonitrile (3.5 ml) and 40% aqueous hydrofluoric acid (0.5 ml). After 3 hours, the mixture was rendered basic with 2N sodium hydroxide solution and worked up (ethyl acetate) to give the crude intermediate desilylated product as an oil. This was dissolved in dichloromethane (4 ml) and pyridinium chlorochromate (0.2 g) was added. The mixture was stirred for 90 minutes and then diluted with ether and filtered through celite. The filtrate was concentrated in vacuo to give the crude intermediate VIII ($R^3$=6-methyl-6-hydroxy-1-heptyl) as an oil. This was dissolved in dry THF and treated with trimethylsilylimidazole (150 mg). After stirring for 3 hours, the mixture was partially concentrated in vacuo, and the residue was purified by chromatography (silica gel, 20% ether in petroleum ether as eluant) to give the intermediate VIII ($R^3$=6-methyl-6-(trimethylsilyloxy)-1-heptyl) as an oil. A solution of this (60 mg) in dry THF (2 ml) was added at $-70°$ C. under $N_2$ to a preformed solution of the lithe-derivative of IX. [This was prepared by adding n-BuLi (1.3M in hexanes, 0.15 ml) to a solution of compound IX (110 mg) in dry THF (2 ml) at $-70°$ C. under $N_2$ and stirring at this temperature for 15 minutes]. After 1 hour, the reaction mixture was worked up (ether) and the residue purified by chromatography (silica gel, 5% ether in petroleum ether as eluant) to give the title compound, identical to material prepared in Preparation 11.

EXAMPLE 1

1(S),3(R)-Dihydroxy-20(S)-(5-hydroxy-5-methyl-1-hexyloxy)-9,10-seco-pregna-5(Z),7(E),10(19)-triene
(Compound 101)

Compound 12 (50 mg) was dissolved in a mixture of acetonitrile (5 ml) and ethyl acetate (1 ml). A 5% solution of HF in acetonitrile/water 8:1 (2 ml) was added, and the solution was stirred under $N_2$ for 40 minutes.

Ethyl acetate (50 ml) was added, and the mixture was extracted with saturated aqueous sodium bicarbonate (10 ml) and water (10 ml), dried and concentrated in vacuo. The residue was purified by chromatography (silica gel, ethyl acetate as eluant) to give the title compound.

NMR: δ=0.53 (s, 3H), 1.15 (d, 3H), 1.21 (s, 6H), 1.2–2.1 (m, 22H), 2.32 (dd, 1H), 2.60 (dd, 1H), 2.82 (dd, 1H), 3.21 (m, 2H), 3.56 (m, 1H), 4.22 (m, 1H), 4.43 (m, 1H), 4.99 (bs, 1H), 5.33 (m, 1H), 6.02 (d, 1H), 6.37 (d, 1H) ppm.

EXAMPLE 2

1(S),3(R)-Dihydroxy-20(S)-(4-hydroxy-4-ethyl-1-hexyloxy)-9,10-seco-pregna-5(Z),7(E),10(19)-triene (Compound 102)

The compound was prepared using the procedure of Example 1, but substituting compound 13 for compound 12.

NMR in agreement with structure.

EXAMPLE 3

1(S),3(R)-Dihydroxy-20(S)-(6'-hydroxy-6'-methyl-1'-heptyloxy-9,10- seco-pregna-5(Z),7(E),10(19)-triene (Compound 103)

The compound was prepared using the procedure of Example 1, but substituting compound 14 for compound 12.

NMR in agreement with structure.

EXAMPLE 4

Capsules containing Compound 101

101 was dissolved in arachis oil to a final concentration of 10 μg 101/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 μl of the 101 in oil solution, such that each capsule contained 1.0 μg 101.

EXAMPLE 5

Dermatological Cream Containing Compound 101

In 1 g almond oil was dissolved 0.5 mg 101. To this solution was added 40 g of mineral oil and 20 g of self-emulsifying beeswax. The mixture was heated to liquify. After the addition of 40 ml hot water, the mixture was mixed well. The resulting cream contains approximately 5 μg of 101 per gram of cream.

What we claim is:

1. A compound of the formula I

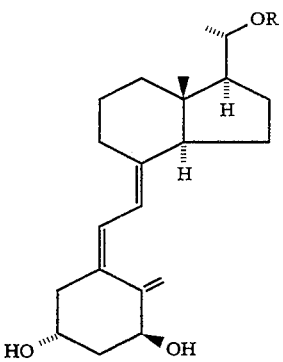

in which formula R stands for an alkyl or cycloalkyl group containing from 7 to 12 carbon atoms optionally substituted with a hydroxy group; and derivatives of the compounds of formula I in which one or more hydroxy groups have been transformed into —O-acyl or —O-glycosyl or phosphate ester groups, these groups being hydrolyzable in vivo.

2. A compound according to claim 1, in which R is a group of formula II

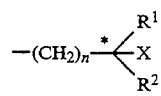

where n is an integer from 1 to 7; $R^1$ and $R^2$ which may be the same or different, stand for hydrogen, $C_1$–$C_5$-alkyl, $C_3$–$C_7$-cycloalkyl, or taken together with the carbon atom (starred in formula II) bearing the group X, $R^1$ and $R^2$ may form a $C_3$–$C_8$ carbocyclic ring; and X stands for hydroxy or hydrogen.

3. A diastereoisomer of a compound according to claims 1 or 2, in pure form; or a mixture of diastereoisomers of a compound according to claim 1 or 2.

4. A compound according to claim 1 which is 1(S),3(R)-dihydroxy-20(S)-(5'-hydroxy-5'-methyl-1'-hexyloxy)-9,10-secopregna-5(Z),7(E),10(19)-triene.

5. A pharmaceutical composition containing an effective amount of one or more of the compounds of claim 1, together with pharmaceutically acceptable, non-toxic carriers.

6. A pharmaceutical composition according to claim 5 in dosage unit form.

7. A dosage unit according to claim 6 containing from 0.5–500 μg of a compound of formula I.

8. A dosage unit according to claim 7 containing from 1–250 μg of a compound according to Formula 1.

* * * * *